US011311706B2

(12) United States Patent
Layer et al.

(10) Patent No.: US 11,311,706 B2
(45) Date of Patent: *Apr. 26, 2022

(54) NASAL IRRIGATION ASSEMBLY AND SYSTEM

(71) Applicant: Preva, LLC, Weston, FL (US)

(72) Inventors: James Layer, Cooper City, FL (US); Keith Rubin, Ft. Lauderdale, FL (US); Alex Desimone, Ft. Lauderdale, FL (US); Jon Buzzard, Boca Raton, FL (US); Ken Solovay, Weston, FL (US)

(73) Assignee: PREVA, LLC, Weston, FL (US)

( * ) Notice: Subject to any disclaimer, the term of this patent is extended or adjusted under 35 U.S.C. 154(b) by 208 days.

This patent is subject to a terminal disclaimer.

(21) Appl. No.: 16/391,938

(22) Filed: Apr. 23, 2019

(65) Prior Publication Data

US 2019/0314621 A1 Oct. 17, 2019

Related U.S. Application Data

(63) Continuation-in-part of application No. 15/072,976, filed on Mar. 17, 2016, now Pat. No. 10,265,462, (Continued)

(51) Int. Cl.
*A61M 31/00* (2006.01)
*A61M 3/02* (2006.01)
*A61M 39/24* (2006.01)

(52) U.S. Cl.
CPC .......... *A61M 31/00* (2013.01); *A61M 3/0258* (2013.01); *A61M 3/0283* (2013.01); *A61M 39/24* (2013.01); *A61M 2210/0618* (2013.01)

(58) Field of Classification Search
CPC .... A61M 31/00; A61M 3/0283; A61M 39/24; A61M 3/0258; A61M 2210/0618;
(Continued)

(56) References Cited

U.S. PATENT DOCUMENTS 2,566,806 A 9/1951 Miller
3,429,313 A 2/1969 Romanelli
(Continued)

FOREIGN PATENT DOCUMENTS

CH 691885 A5 11/2001
EP 197778 A1 8/2008
(Continued)

OTHER PUBLICATIONS

Carrasquilla, et al; Chemistry a European Journal Communication, "Patterned Paper Sensors Printed with Long-Chain DNA Aptamers" 2015, 21, 7369-7373, Wiley Online Library.
(Continued)

*Primary Examiner* — Lauren P Farrar
*Assistant Examiner* — Hamza A Darb
(74) *Attorney, Agent, or Firm* — Malloy & Malloy, PL

(57) ABSTRACT

An assembly for nasal irrigation for the handheld irrigation of a user's nasal cavity comprising a housing with a refill chamber containing irrigating fluid, an applicator, an actuator for forcing irrigating fluid from the refill chamber through the applicator into the user's nasal cavity during operation, and a solution port for refilling the refill chamber. Some embodiments of the present invention may further comprise a system for nasal irrigation that includes the assembly for nasal irrigation or handheld irrigator, as well as a solution assembly structured for dispensing irrigating fluid to the handheld irrigator, a docking station for removably housing the handheld irrigator, a solution assembly and a refill control, including a check valve.

16 Claims, 16 Drawing Sheets

Related U.S. Application Data which is a continuation-in-part of application No. 14/180,002, filed on Feb. 13, 2014, now Pat. No. 9,289,547.

(58) Field of Classification Search
CPC .... A61M 2209/086; A61M 2205/8206; A61M 3/0287; A61H 2201/1604; A61H 2205/023; A61H 35/04
See application file for complete search history.

(56) References Cited

U.S. PATENT DOCUMENTS

| | | | |
|---|---|---|---|
| 4,294,251 A | 10/1981 | Greenwald et al. | |
| 4,457,747 A | 7/1984 | Tu | |
| 4,655,197 A * | 4/1987 | Atkinson | A61M 3/0208 601/161 |
| 4,663,628 A | 5/1987 | Duncan et al. | |
| 4,790,979 A | 12/1988 | Terminiello et al. | |
| 4,904,238 A | 2/1990 | Williams | |
| 4,924,862 A | 5/1990 | Levinson | |
| 4,998,915 A | 3/1991 | Hannah | |
| 5,009,634 A | 4/1991 | Feldman et al. | |
| 5,277,175 A | 1/1994 | Riggs et al. | |
| 5,505,193 A | 4/1996 | Ballini et al. | |
| 5,542,918 A | 8/1996 | Atkinson | |
| 5,649,530 A | 7/1997 | Ballini | |
| 6,022,748 A | 2/2000 | Charych et al. | |
| 6,135,358 A | 10/2000 | Ballini | |
| 6,145,703 A | 11/2000 | Opperman | |
| 6,736,792 B1 | 5/2004 | Liu | |
| 6,907,879 B2 | 6/2005 | Drinan et al. | |
| 7,063,686 B2 | 6/2006 | Mezzoli | |
| 7,080,980 B2 | 7/2006 | Klupt | |
| 7,143,763 B2 | 12/2006 | Abate | |
| 7,569,031 B2 | 8/2009 | Britto | |
| 7,959,597 B2 | 6/2011 | Baker et al. | |
| 7,981,077 B2 | 7/2011 | Hoke et al. | |
| 8,048,023 B2 | 11/2011 | Hoke et al. | |
| 8,343,114 B2 | 1/2013 | Mehta | |
| 9,289,547 B2 | 3/2016 | Layer et al. | |
| 9,433,724 B2 | 9/2016 | Rubin et al. | |
| 10,265,462 B2 | 4/2019 | Layer et al. | |
| 2003/0069549 A1 | 4/2003 | Macmahon et al. | |
| 2003/0089367 A1 | 5/2003 | Abate | |
| 2003/0158527 A1 | 8/2003 | Mezzoli | |
| 2003/0172925 A1 | 9/2003 | Zocca et al. | |
| 2004/0182388 A1 | 9/2004 | Djupesland | |
| 2005/0004498 A1 | 1/2005 | Klupt | |
| 2005/0011282 A1 | 1/2005 | Voege et al. | |
| 2007/0149922 A1 | 6/2007 | Schneider et al. | |
| 2008/0138842 A1 | 6/2008 | Boehringer et al. | |
| 2008/0154183 A1 | 6/2008 | Baker et al. | |
| 2008/0183128 A1 | 7/2008 | Morriss et al. | |
| 2008/0221507 A1 | 9/2008 | Hoke et al. | |
| 2008/0312674 A1 | 12/2008 | Chen et al. | |
| 2009/0104690 A1 | 4/2009 | Bayliff et al. | |
| 2009/0197283 A1 | 8/2009 | Gold et al. | |
| 2009/0281483 A1 * | 11/2009 | Baker | A61M 1/784 604/28 |
| 2009/0281485 A1 | 11/2009 | Baker et al. | |
| 2010/0016787 A1 * | 1/2010 | Shapiro | A61M 3/0208 604/31 |
| 2010/0152653 A1 * | 6/2010 | Hoke | A61M 3/0258 604/94.01 |
| 2011/0132369 A1 | 6/2011 | Sanchez | |
| 2011/0144588 A1 | 6/2011 | Taylor et al. | |
| 2011/0220119 A1 | 9/2011 | Lowenstein et al. | |
| 2012/0135437 A1 | 5/2012 | Brennan et al. | |
| 2012/0179118 A1 | 7/2012 | Hair | |
| 2013/0012869 A1 | 1/2013 | Cha et al. | |
| 2013/0137598 A1 | 5/2013 | Verschoor et al. | |
| 2013/0244314 A1 | 9/2013 | Yuki et al. | |
| 2014/0121592 A1 | 5/2014 | Rubin et al. | |
| 2014/0193925 A1 | 7/2014 | Bhattacharyya et al. | |
| 2014/0200507 A1 | 7/2014 | Azeez | |
| 2014/0275857 A1 | 9/2014 | Toth et al. | |
| 2014/0371690 A1 | 12/2014 | Sprada et al. | |
| 2015/0118689 A1 | 4/2015 | Egan et al. | |
| 2016/0054310 A1 | 2/2016 | Brennan et al. | |
| 2016/0303308 A1 | 10/2016 | Layer et al. | |
| 2016/0375192 A1 | 12/2016 | Rubin et al. | |
| 2020/0188575 A1 | 6/2020 | Rubin et al. | |
| 2020/0297915 A1 | 9/2020 | Rubin et al. | |

FOREIGN PATENT DOCUMENTS

| | | |
|---|---|---|
| EP | 2389918 | 11/2011 |
| EP | 2389918 A1 | 11/2011 |
| EP | 2914312 B1 | 8/2017 |
| JP | 2010520033 | 6/2010 |
| JP | 2010527636 | 8/2010 |
| WO | WO2008058160 | 5/2008 |
| WO | WO2008109726 | 9/2008 |
| WO | WO2010126586 | 11/2010 |
| WO | WO 2011/127407 | 10/2011 |
| WO | WO 2014/070854 | 5/2014 |
| WO | WO 2015/123276 | 8/2015 |

OTHER PUBLICATIONS

Liu, et al; Angewandte Chemie, "Target-Induced and Equipment-Free DNA Amplification With a Simple Paper Device" 2016, 128, 2759-2763, Wiley Online Library.

Translation EP-238918-A1, EPO Patent Translate, translated Mar. 2, 2019.

* cited by examiner

NASAL IRRIGATION ASSEMBLY AND SYSTEM

CLAIM OF PRIORITY

The present application is a continuation-in-part application of U.S. patent application Ser. No. 15/072,976, filed on Mar. 17, 2016, now U.S. Pat. No. 10,265,462, which issued Apr. 23, 2019, which was a continuation-in-part of application Ser. No. 14/180,002, filed on Feb. 13, 2014, now U.S. Pat. No. 9,289,547, which issued on Mar. 22, 2016, and is incorporated herein by reference.

BACKGROUND OF THE INVENTION

Field of the Invention

This invention is directed to an irrigation assembly and system for irrigation of a user's nasal cavity using a refillable irrigation solution.

Description of the Related Art

Poor nasal hygiene is a common problem existing and prevalent in individuals of all ages and can lead to nasal and sinus disease. Such disease, including congestion, infection, and other pathologic conditions of the nasal passages and paranasal sinuses, is typically caused by viruses, bacteria and other microbes and/or exposure to environmental allergens. Sinonasal disease is one of the most common medical conditions in the United States, afflicting approximately 33 million people and accounting for over $5.8 billion in healthcare costs annually ("Nasal Congestion: More than physical obstruction," Science Daily, Oct. 17, 2011). Nasal congestion and the associated feeling of obstruction is the symptom that typically causes individuals to seek medical assistance. Common signs and symptoms arising from poor nasal hygiene include nasal inflammation, rhinorrhea, sinusitis, irritation, pain and nasal passage blockage. Medications used to treat nasal pathology inherently include potential side effects and possibly excessive costs.

A number of studies demonstrate that regular use of nasal irrigation is an effective therapy in the relief of symptoms associated with poor nasal hygiene (e.g. Rabago et. al, Journal of Family Practice. 2002; 51(12):1049-1055; Tomooka et. al, Laryngoscope. 2000 July; 110(7):1189-93.) Other similarly related clinical studies indicate that nasal wash with isotonic saline can improve certain infection outcomes (Slapak et. al, Archives of Otolaryngology-Head & Neck Surgery. 2008; January; 134(1):67-74) and that regular nasal irrigation is a beneficial therapy for the treatment of allergy related symptoms (e.g. Garavello et. al, Pediatr Allergy Immunol. 2003 April; 14(2):140-3.) Accordingly, these studies indicate that nasal irrigation is a clinically proven method of improving sinus related disease, including allergies and infections. Current standard of care for nasal irrigation involves exposing the nasal cavity and passages to a streaming volume of saline or other prophylactic or therapeutic solutions. In addition to cleansing the nasal cavities of pathogens and allergens, such irrigation related treatment is also believed to include a number of physiological effects. These include stimulation of mucosal cilia and increasing physiologic flow of mucous, which individually or in concert may reduce the risk of nasopharyngeal and sinus localization of pathogens and allergens, thereby reducing potential morbidity and mortality. Further, irrigation therapy that includes rinsing of the interior of the nasal cavity, typically washes away waste, microbial byproducts, and/or encrustations, which may be a causal factor in a number of undesirable conditions and symptoms. Conventional irrigation techniques are intended to keep sinus cavities, nasal passages, and the drainage from sinuses to nasal passage in a healthy state. Improving nasal hygiene with irrigation thus reduces the likelihood that the nasal cavity, paranasal sinuses, and related structures will become colonized with pathogens, thereby reducing the potential for morbidity and mortality.

As conventionally practiced, nasal irrigation is known to apply and utilize various types of manually or automatically operated irrigation and/or nasal aspirators. As such, irrigating fluid is applied in a manner or in such volume sufficient to flood the nasal cavity in an attempt to remove the aforementioned pathogens, allergens, encrustations, or waste after the application of the irrigating fluid has been completed. However, disadvantages at least partially associated with the flooding of the nasal cavity, occur when the irrigating and aspirating steps are conducted separately or successively, which can lead to suboptimal cleansing and disinfection. As typically operated, existing manual devices serve to sequentially, rather than simultaneously, deliver an irrigation agent to the nasal cavity followed by a subsequent and frequently delayed aspiration of the agent and accumulated waste.

Additionally, irrigation devices that flood the nasal cavity and sinuses can create a cumbersome, uncomfortable, and aesthetically unappealing experience for the user. For example, the flooding irrigant may create a drowning sensation for the user and waste fluid may travel around the nasal septum and drain out the same or opposite nostril, thereby spilling waste fluid onto a user's face and/or clothes. In flooding of the nasal passage a user may also experience the unpleasant taste of irrigant in the back of their throat. These devices are therefore unacceptable to many users and observers.

On the other end of the spectrum, irrigation/suction devices that do not flood the nasal cavity often infuse minimal fluids, typically in a mist that is insufficient to remove encrustations and other contaminants.

Other manual irrigation devices frequently involve the use of a conventionally structured bulb-type syringe. The ineffectiveness of such devices are well known and recognized as being generally associated with inadequate negative pressure and resulting inadequate removal of the waste fluid and waste materials contained within the nasal cavity or passages. Also, manual irrigation and suction devices may include dimensional and/or configurational characteristics which could possibly result in damage to the interior of the nasal cavity.

Irrigation devices that do not solely moisten the mucosa and provide sufficient flow to dislodge encrustations and contaminants (e.g. the neti pot and many commercially available nasal irrigation devices), require fluid to be added to the device from an external source, often tap water or bottled water. Such water may be contaminated with pathogenic microbes or other agents that can be infused into the nasal cavity and sinuses and cause infections, even death ("Primary Amebic Meningoencephalitis Deaths Associated With Sinus Irrigation Using Contaminated Tap Water", Yoder, et. al, Journal of Clinical Infectious Diseases, Aug. 22, 2012, Epub ahead of print). In addition, prior to irrigation, such fluid often needs to be manually mixed with a salt powder or other solute which can be time consuming and inconvenient.

For devices that interface with sealed fluid containers (U.S. Pat. No. 7,981,077) that are manually opened and fastened to the device, the manual attachment of the container can also cause inadvertent contamination. Also, because of suboptimal use of space within device housings, devices that collect waste fluid either capture only a small volume of such fluid or capture a larger volume of waste fluid, but do so at the expense of having to be unnecessarily bulky and require the presence of an additional collection reservoir.

Therefore, there is a need for an effective, convenient, efficient, and aesthetically pleasing irrigation assembly preferably in the form of a reuseable and refillable irrigation assembly or handheld irrigator that may be refilled with sterile or non-contaminated fluid. Moreover, such an irrigation assembly should be operative to accomplish delivery of an irrigating fluid, possibly including a cleaning, disinfecting, or other agent, to the nasal cavity and passages and the concurrent aspiration of the waste fluid and waste material there from. Concurrent irrigation and aspiration would then overcome many of the problems of existing devices and serve to effectively provide both a sufficient pressure applied to the irrigating fluid and a significant negative pressure applied to the waste fluid to better accomplish an improved irrigation therapy. A preferred embodiment of the present invention may comprise a system further including a docking station and solution assembly to facilitate the recharging and/or refilling of the irrigation assembly.

SUMMARY OF THE INVENTION

The present invention is directed to a system and assembly structured for the irrigation of a user's nasal cavity and passages in order to promote and maintain better nasal hygiene by effectively cleaning, disinfecting and/or medicating the nasal cavity and passages. More specifically, one embodiment directed to the irrigation system may comprise a docking station, an irrigation assembly or handheld irrigator, and a solution assembly.

The docking station is operatively structured to allow for the refilling of irrigating fluid from the solution assembly into the irrigation assembly or handheld irrigator. As such, the docking station comprises a first recess structured to receive the handheld irrigator, and a second recess structured to receive the solution assembly. The docking station may comprise a delivery assembly, such as a fluid pump, to effect the refilling of irrigating fluid or otherwise cause the irrigating fluid to flow from the solution assembly into the handheld irrigator. The docking station may further comprise at least one microbial assembly, such as UV light, to inhibit or prevent microbial growth on the handheld irrigator, as well as storage compartment(s) for the handheld irrigator's applicator(s).

The solution assembly comprises a container and a dispensing assembly. The container may be removable or may be of a one-piece construction as part of the solution assembly. In at least one embodiment, the container may comprise a removable and disposable container. The disposable container may hold aseptically prefilled irrigating solution. Other embodiments may comprise a reuseable container which may be refilled by a user. The dispensing assembly may be structured and operatively disposed to cooperatively engage with the delivery assembly of the docking station, such as to create a flow of the irrigating fluid from the solution assembly into the handheld irrigator.

The irrigation assembly or handheld irrigator may comprise a housing, a refill chamber, an applicator, an actuator, a solution port, a drain line, a valve assembly, and a user interface. Accordingly, irrigating fluid may be received via the solution port through a refill dispenser such as the solution assembly. Irrigating fluid enters through the solution port and flows into the refill chamber within the housing. In some embodiments an external pump or device such as the delivery assembly of the docking station, or the delivery assembly in cooperation with the dispensing assembly of the solution assembly, forces the flow of the irrigating fluid into the solution port and down to the refill chamber. In other embodiments, the actuator of the handheld irrigator may be structured and configured to draw the irrigating fluid from the refill dispenser without any external force.

The solution port may also be used for the irrigation of a user's nasal cavity, and the actuator may be structured and disposed to force irrigating fluid from the refill chamber into a user's nostril and nasal cavity through the solution port. A valve assembly disposable between an irrigation position and refill position may be coupled to the solution port. The irrigation position allows irrigating fluid to pass from the refill chamber through the solution port and out of the applicator. The refill position allows irrigating fluid to pass from a refill dispenser such as the solution assembly into the refill chamber. The valve assembly may be controllable by a user interface or may be automatic. For instance, when the handheld irrigator is removed from the docking station, the valve assembly may automatically change to the irrigation position. Similarly, when the handheld irrigator is connected to or docked to the docking station, the valve assembly may automatically switch to the refill position. Of course, other embodiments of the present invention may comprise a separate solution port for refilling irrigating fluid into the handheld irrigator, and an irrigation port for forcing the irrigating fluid out of the handheld irrigator. In these embodiments a valve assembly may be omitted.

Waste fluid that drains back down a user's nostrils may be collected by the applicator and drained down through a separate drain line, to be dispersed outside the housing of the handheld irrigator, which may then conveniently fall into a sink during user operation. The applicator may be detachable and various different applicator(s) may be switched in and out based on user preference.

The actuator of the handheld irrigator may comprise a fluid pump, inflatable bladder, or alternatively a spring injected piston. The actuator may be powered by an internal power supply, an external power supply, by pressurized gas, or by mechanical force or manual control. A user interface may be coupled or connected to the actuator and control its operation. For instance, a user may be able to switch on and off the actuator, to change the speed and pulse of the flow, and may even affect the direction of the flow.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
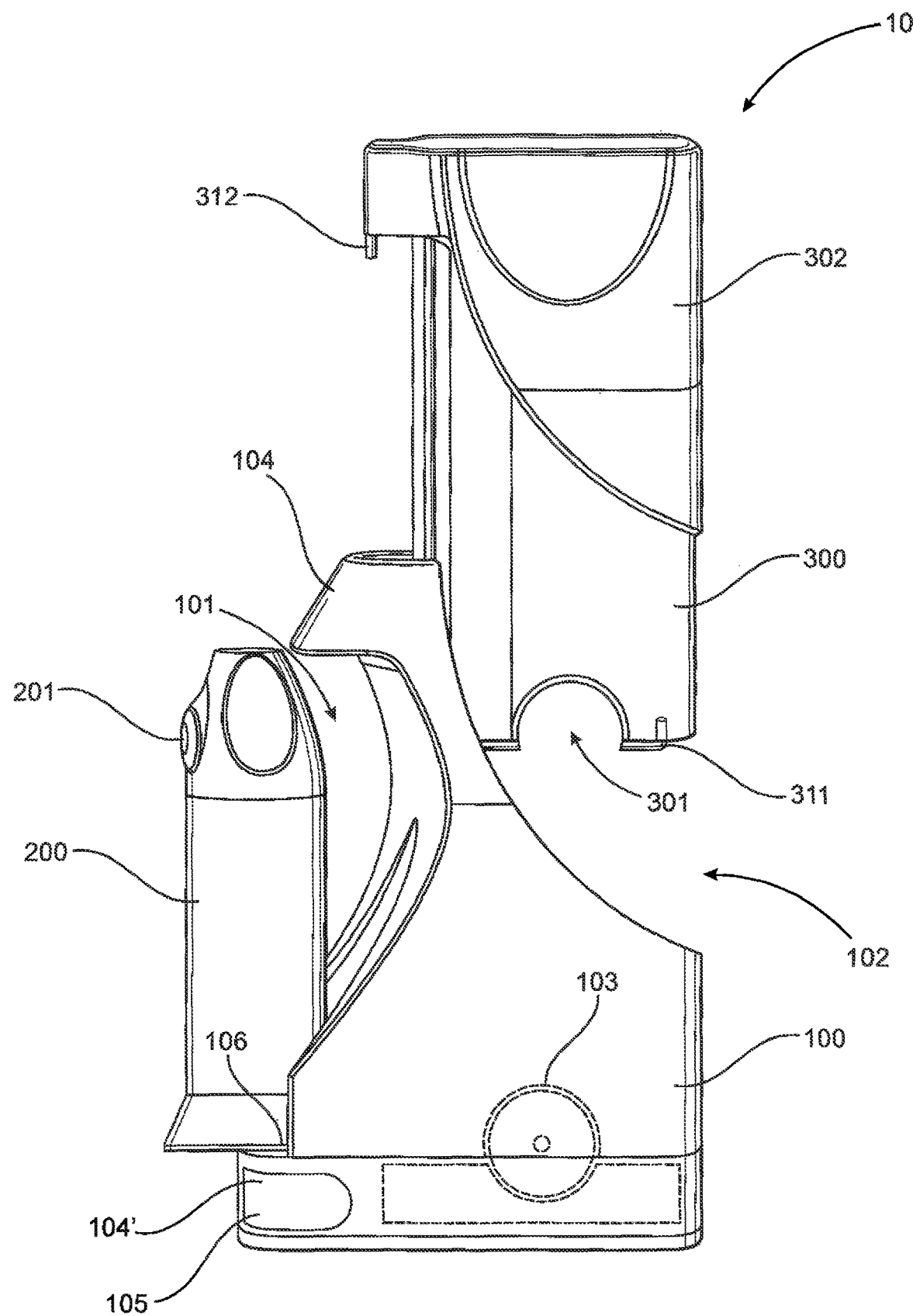
FIG. 1 is a schematic view of the irrigation system of the present invention illustrating its removable components.

As clearly represented in the accompanying drawings, the present invention is directed to an irrigation system generally indicated as 10 for the irrigation of a user's nasal cavity and passages in order to promote and maintain better nasal hygiene. The irrigation system 10 may comprise a docking station 100, an irrigation assembly or handheld irrigator 200, and a solution assembly 300.

More specifically, the docking station 100 may comprise a first recess 101 structured to removably receive the handheld irrigator 200, as well as a second recess 102 structured to removably receive the solution assembly 300. As such, the docking station 100 is operatively structured to allow for the refilling of irrigating fluid from the solution assembly 300 to the handheld irrigator 200. In at least one embodiment, the docking station may comprise a delivery assembly 103 to effect the refilling of irrigating fluid, or to otherwise force irrigating fluid from the solution assembly 300 into the handheld irrigator 200.

Delivery assembly 103 may comprise a fluid pump, such as a peristaltic pump or any other positive displacement pumps. In other embodiments, the delivery assembly 103 may comprise impulse pumps, velocity pumps, diaphragm pump, gear pump, bellows pump, impeller pump, gravity pumps, steam pumps, valveless pumps, or any other pumps or other device appropriate for creating liquid flow or movement. Delivery assembly 103 may comprise a motorized pump which may be powered by electricity through the docking station 100, whether battery-enabled or through any AC or DC current. Alternatively, delivery assembly 103 may also comprise a driven piston, which may be manually driven, spring-driven or may be driven by pressure created by a gas canister such as the $CO_2$ canister 150 of FIG. 3. It should also be noted that in some other embodiments, delivery assembly 103 may be omitted, where the handheld irrigator 200 may be capable of drawing out irrigation solution from the solution assembly 300, for instance through its actuator which may serve to create a suction force. Of course other pressurized mechanisms such as diaphragm pumps, fluid pumps and/or pressurized gas systems may be used. Additionally, a gravity feed could be used to transfer fluid to the handheld. In embodiments comprising a gas canister such as the $CO_2$ canister 150, the canister may also be utilized to carbonate the irrigating fluid within either the handheld irrigator 200 or the solution assembly 300, which may enhance the irrigating fluid and also serve as a microbial inhibitor.

Figure 4A:
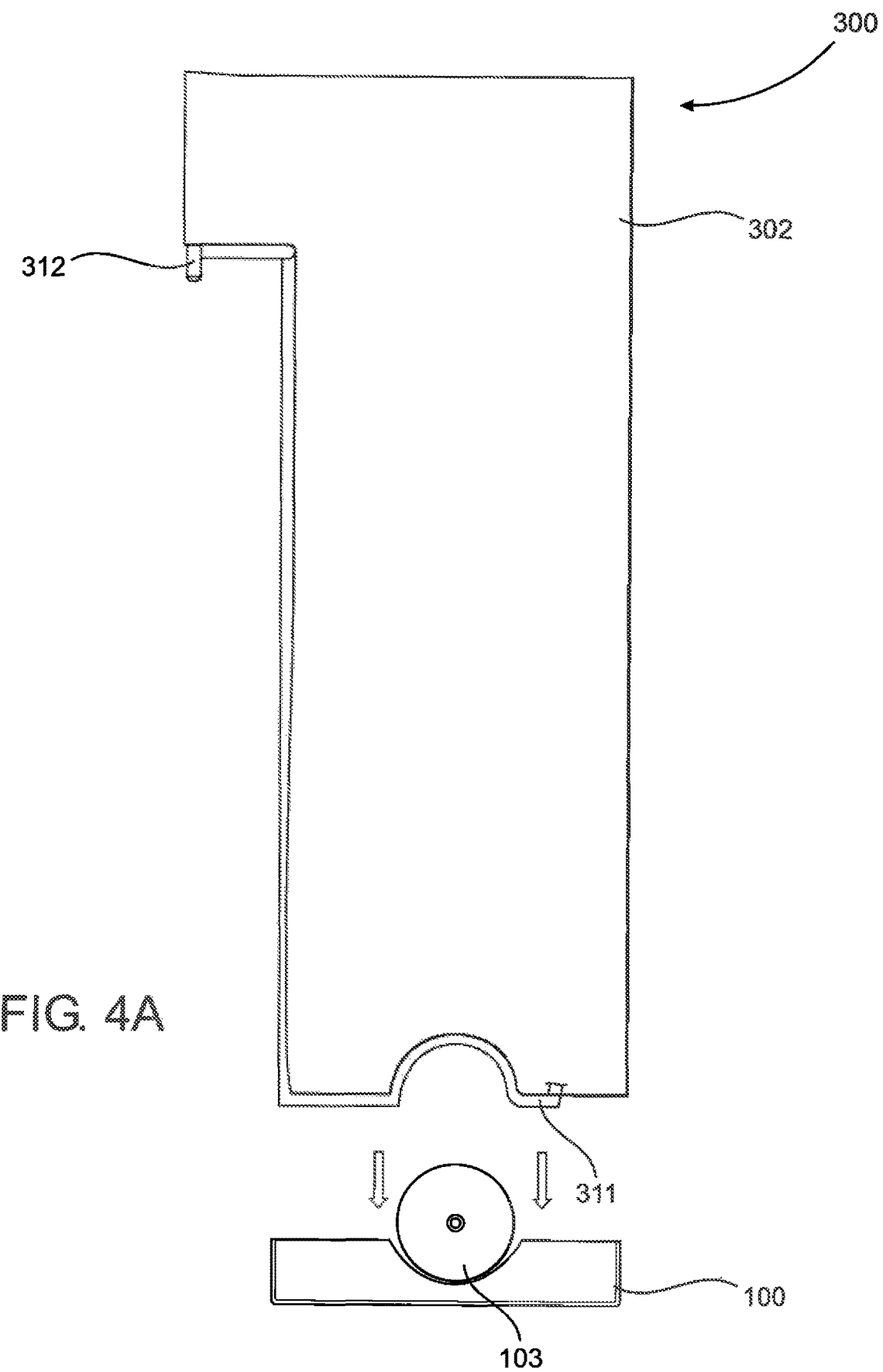
FIGS. 4A and 4B are schematic views of one embodiment of the solution assembly of the present invention.
Figure 4B:
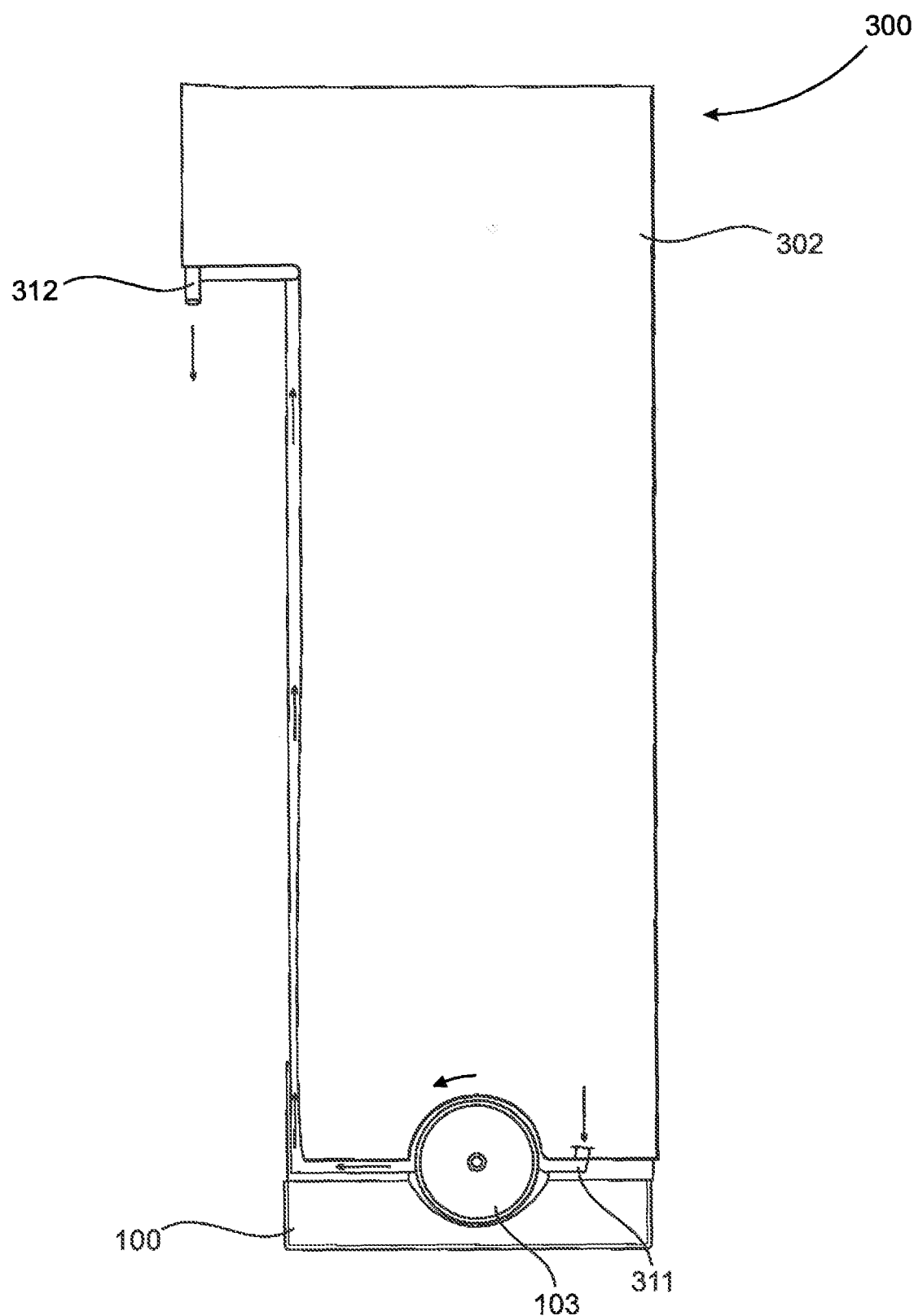

In at least one embodiment, the second recess 102 may be operatively structured and disposed to allow delivery assembly 103 to interact with the dispensing assembly 301 of the solution assembly 300 in order to create a flow of the irrigating solution from the solution assembly 300 into the handheld irrigator 200. As set forth above the delivery assembly may comprise, but is not limited to, a peristaltic pump or a portion thereof as represented in FIGS. 4A and 4b. Of course, any other types of positive displacement pumps or other fluid pumps known to those skilled in the art may be used. Accordingly, the delivery assembly 103 may interface with the dispensing assembly 301 in order to effect the refilling operation, as also illustrated in FIGS. 4A and 4B. The dispensing assembly 301 may comprise a passage at least partially defining a flow path of the irrigating fluid from the container 302 to the handheld irrigator 200. In at least one embodiment, a delivery assembly 103 may cause the irrigating fluid to enter into inlet tube 311 and out through the nozzle 312, into the handheld irrigator 200. The inlet tube 311 and nozzle 312 may be attached to and/or are part of the container 302. The nozzle 312 may mate with the handheld irrigator 200 without contacting the docking station 100, in order to prevent contamination. The nozzle 312 and/or the apical portion of handheld irrigator 200 may further comprise at least one hermetic seal or other seal. This effectively allows the handheld irrigator 200 to be refilled without exposing the irrigating solution to the external environment.

Similarly, the first recess 101 may be operatively structured and disposed to removably receive handheld irrigator 200, with or without the applicator attached. Applicators which are removed or additional applicators may be stored at a storage compartment 105. In at least one embodiment, the docking station 100 may serve as a charging station for the handheld irrigator 200, where the handheld irrigator 200 may have an internal rechargeable power supply powering its actuator. As such, contact strip charging, induction charging, or other methods and components appropriate for the electrical recharging of a device may be used. The first recess 101 may also comprise a positioning assembly 106 structured and configured to sense when the handheld irrigator 200 is docked, and raises the handheld irrigator 200, forcing it to snap into the nozzle 312 of the solution assembly, which may then automatically trigger the refilling of the handheld irrigator 200. The refilling may also stop automatically when the handheld irrigator 200 is full.

Figure 2:
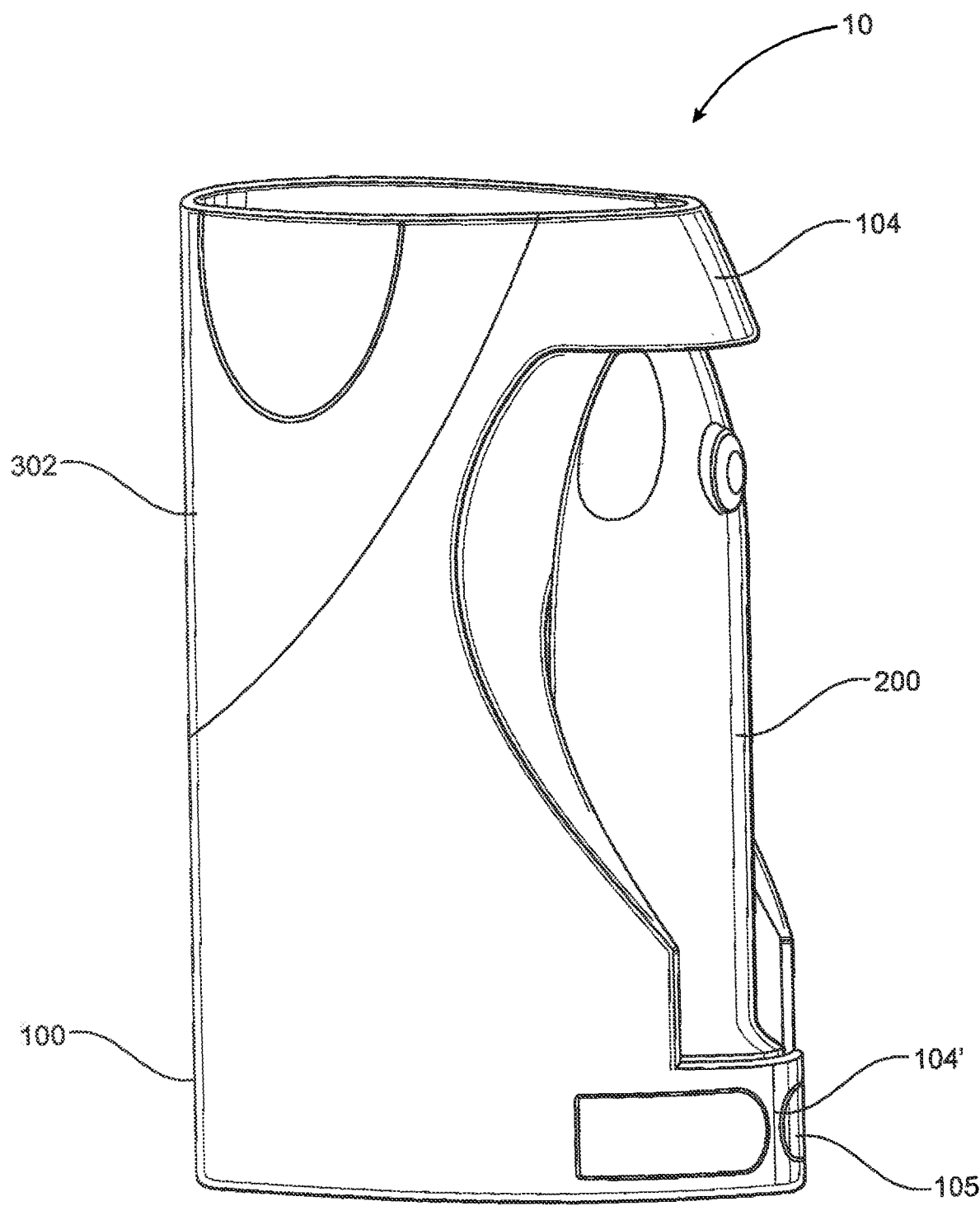
FIG. 2 is a perspective view of the assembled components of the embodiment of FIG. 1.
Figure 3:
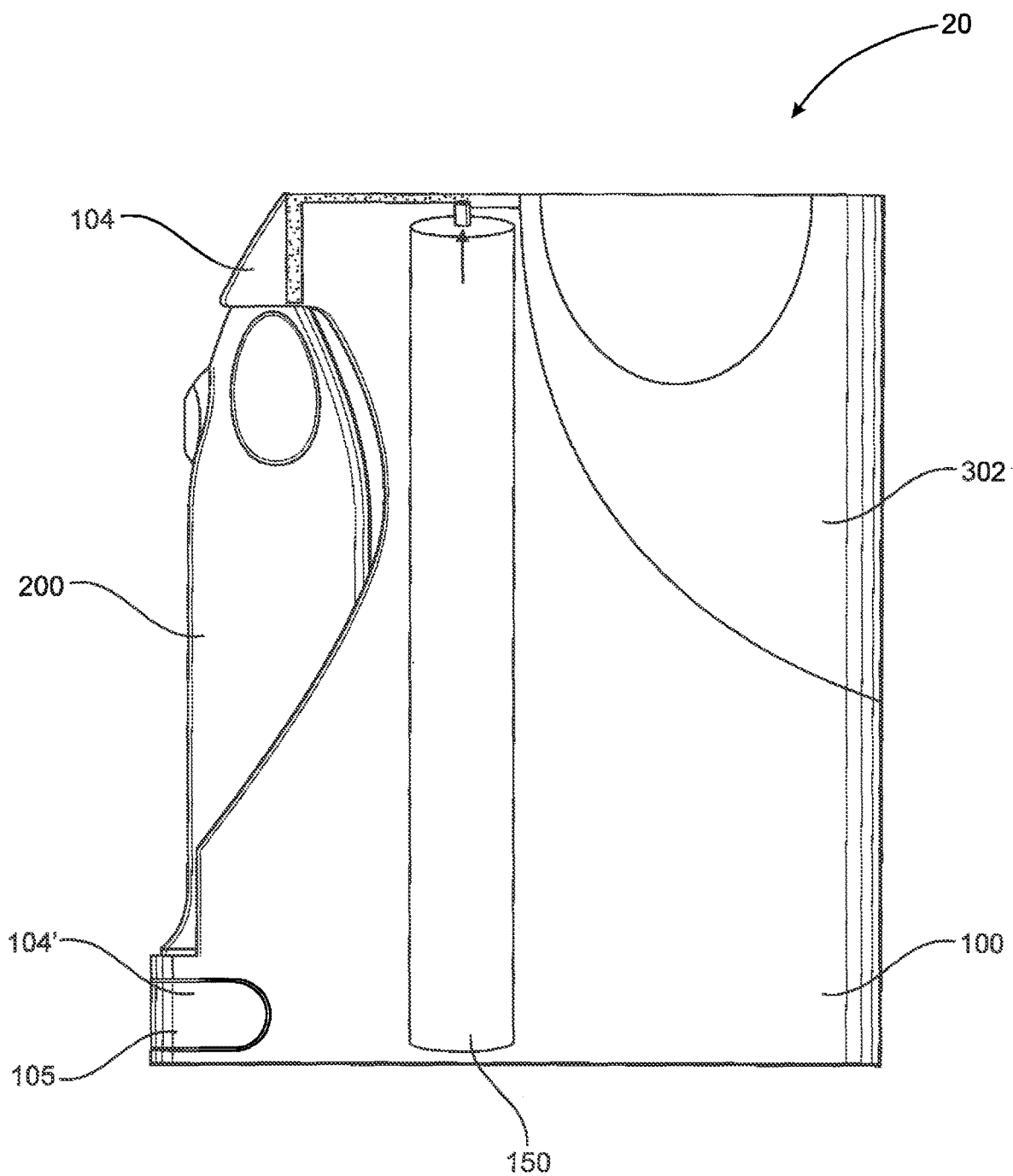
FIG. 3 is a schematic view of an alternative embodiment of the irrigation system.

The docking station 100 may further comprise at least one antimicrobial assembly generally depicted at 104 and 104'. The antimicrobial assembly(s) are structured and disposed to sanitize the applicator(s) of the handheld irrigator 200 as well as the areas surrounding the applicator attachment. As such, and as illustrated by FIGS. 2 and 3, antimicrobial assembly 104 may sanitize the apical portion of the handheld irrigator 200, and antimicrobial assembly 104' may sanitize any stored applicator(s) therein. In at least one embodiment, the antimicrobial assembly 104 and 104' may comprise at least one UV light. However, other antimicrobial assemblies and methods may be used, such as steam disinfection, dry heat disinfection, or filtration.

The container 302 of the solution assembly 300 may be removable or may be of a one-piece construction. In at least one embodiment, the container 302 may comprise a disposable container, which may range in solution volumes from 0.5 to 2L in a preferred embodiment, but may also comprise other volumes. The disposable container may come aseptically prefilled with the irrigating solution, which may comprise sterile or filtered solution, and may be replaced when empty. This prevents bacteria or microbial colonization and ensures safety of the solution. However, in other embodiments a user may refill the container 302 with irrigating solution.

Figure 5:
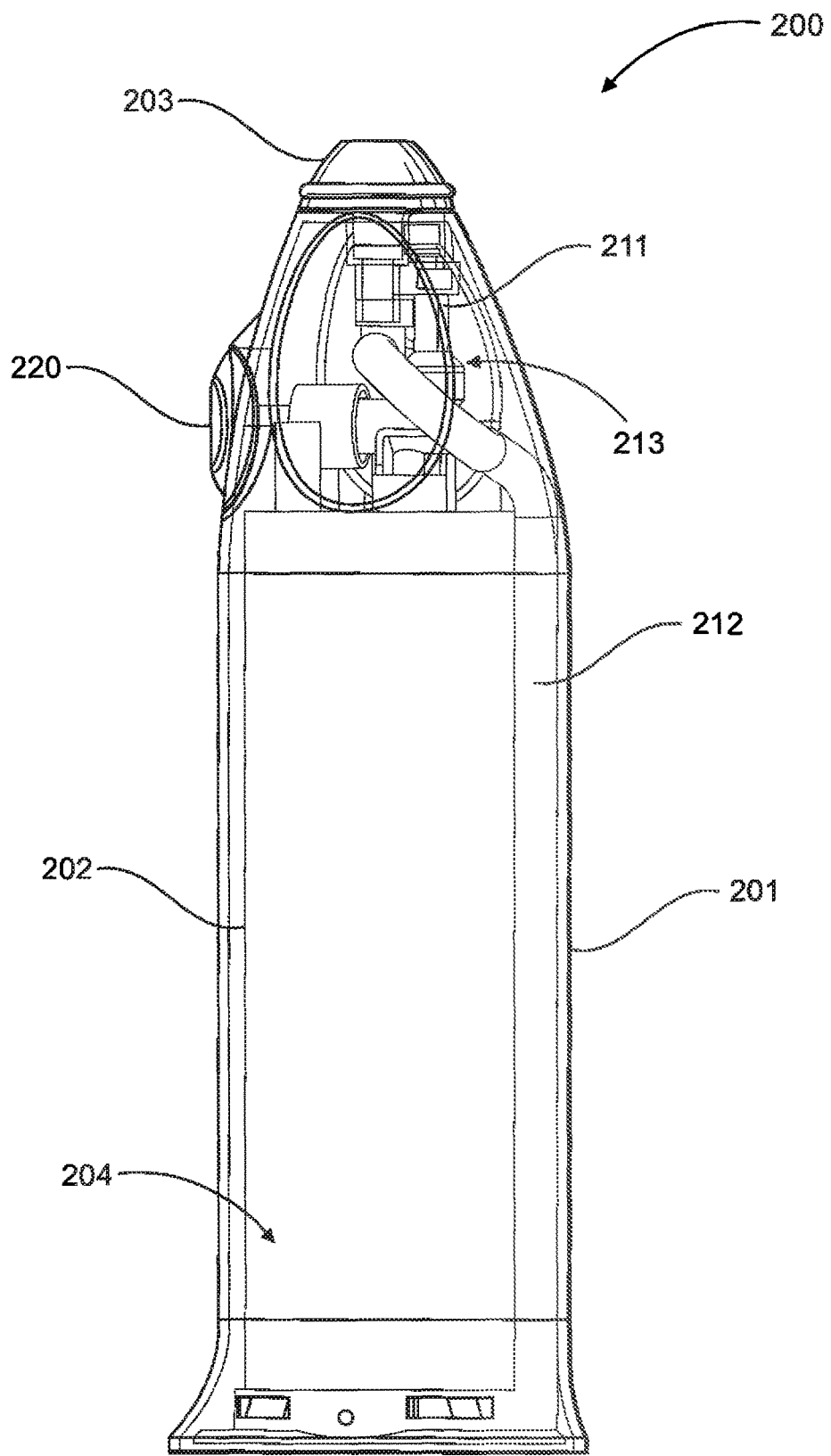
FIG. 5 is a cutaway view of the nasal irrigation assembly of the present invention.

The handheld irrigator 200, dimensioned to be handheld device and/or portable, is depicted in further detail in FIG. 5, and may comprise a housing 201, a refill chamber 202, an applicator 203, an actuator 204, a solution port 211, a drain line 212, a valve assembly 213, and a user interface 220. Accordingly, irrigating fluid may be received via solution port 211 through a refill dispenser such as the solution assembly 300 recited above. Irrigating fluid received through the solution port 211 flows into the refill chamber 202, which is enclosed within housing 201 and is structured to contain the irrigating fluid therein. In some embodiments an external pump or device forces the flow of irrigating fluid into the solution port 211 and down to the refill chamber 202. In other embodiments, the actuator 204 may be structured and configured to draw the irrigating fluid from the refill dispenser and into the refill chamber 202.

In at least one embodiment, the same solution port 211 is also used for irrigation of a user's nasal cavity. As such, the actuator 204 may also be structured, disposed, and/or configured to force irrigating fluid from the refill chamber 202 into a user's nostril and nasal cavity, when the handheld irrigator 200 is in operation. More specifically, irrigating fluid travels from the refill chamber 202 up through the solution port 211 to the applicator 203, there it enters the irrigation inlet 251 according to FIGS. 10 and 11, and is further projected upwards through the aperture(s) 250 and into a user's nostril.

As such, a valve assembly 213 disposable between an irrigation position and refill position may be coupled to the solution port 211. The irrigation position defines a path of fluid flow of the irrigating fluid from the refill chamber 202 to the applicator 203 and into a user's nasal cavity, and the refill position defines a path of fluid flow from the refill dispenser into the refill chamber 202. In at least one embodiment, the valve assembly 213 would be set to the irrigation position when the handheld irrigator 200 is in operation, such as when it is removed from the docking station 300 described earlier above. The irrigation position would ensure a one-way flow during operation and prevent the possibility of contamination from outgoing irrigating fluids or waste fluids that may otherwise drain back into the refill chamber 202.

Figure 13A:
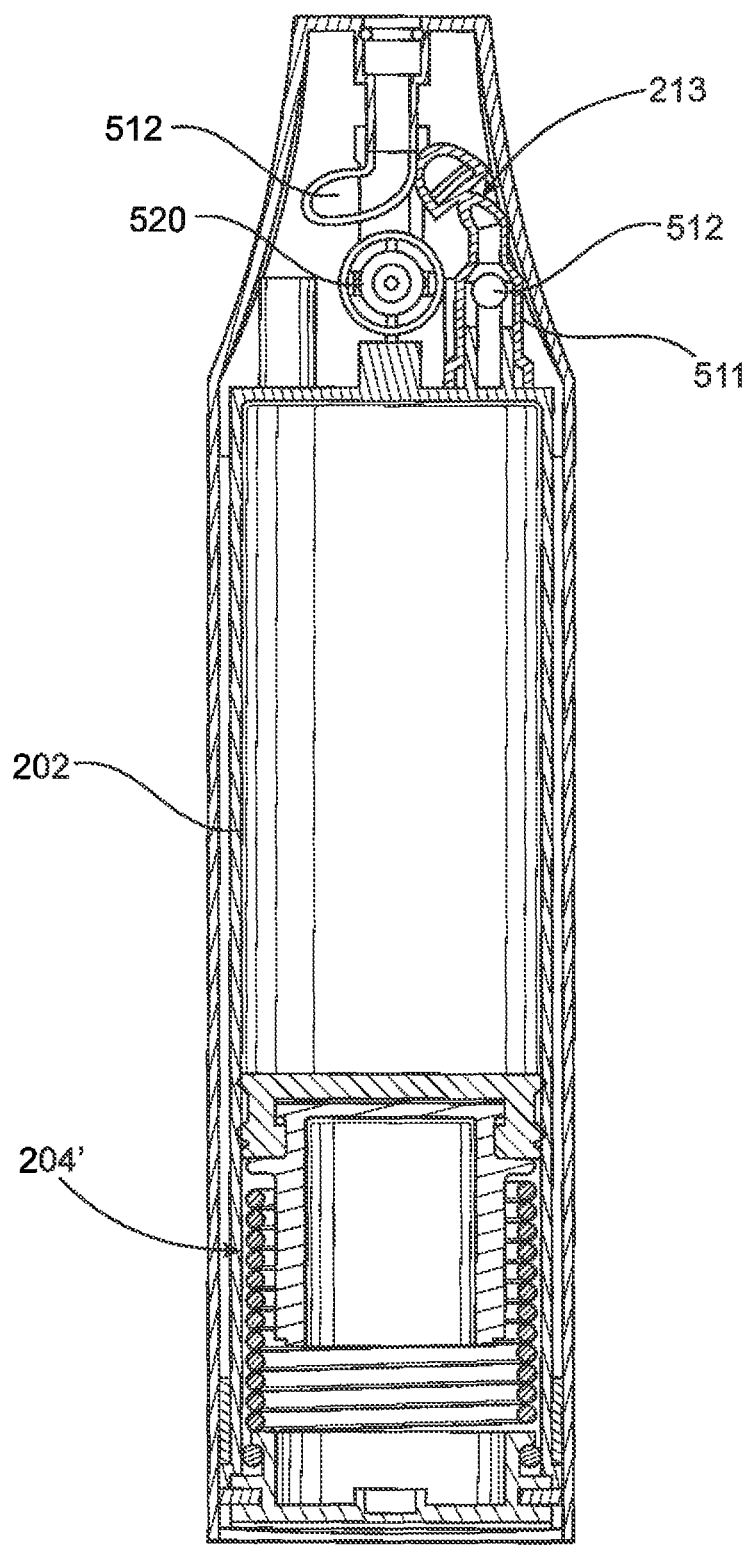
FIG. 13A is a cutaway view of an embodiment of the nasal irrigation assembly comprising a spring-driven piston.
Figure 13B:
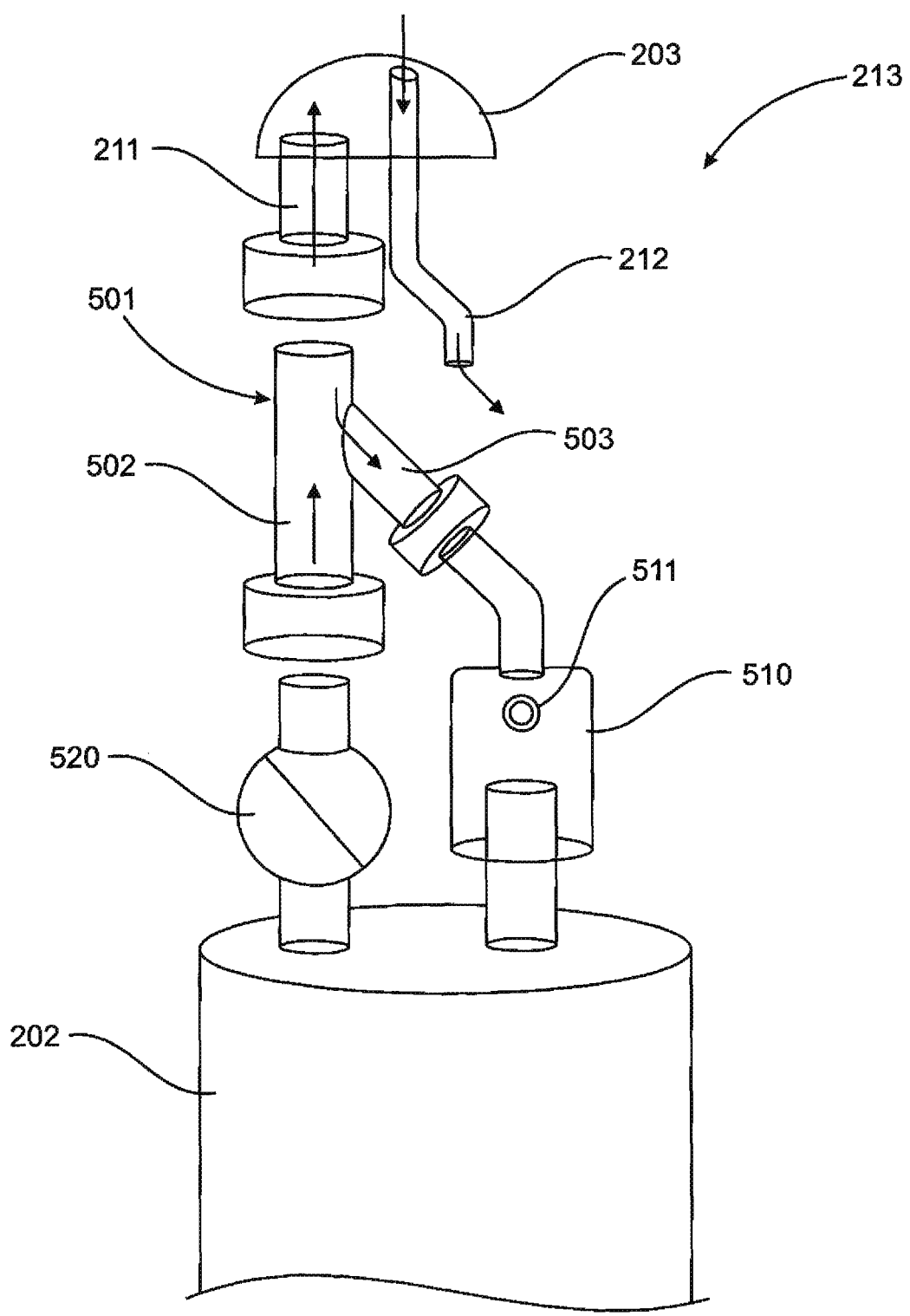
FIG. 13B is a detail schematic view of the valve assembly of the nasal irrigation assembly of FIG. 13A.
Figure 14:
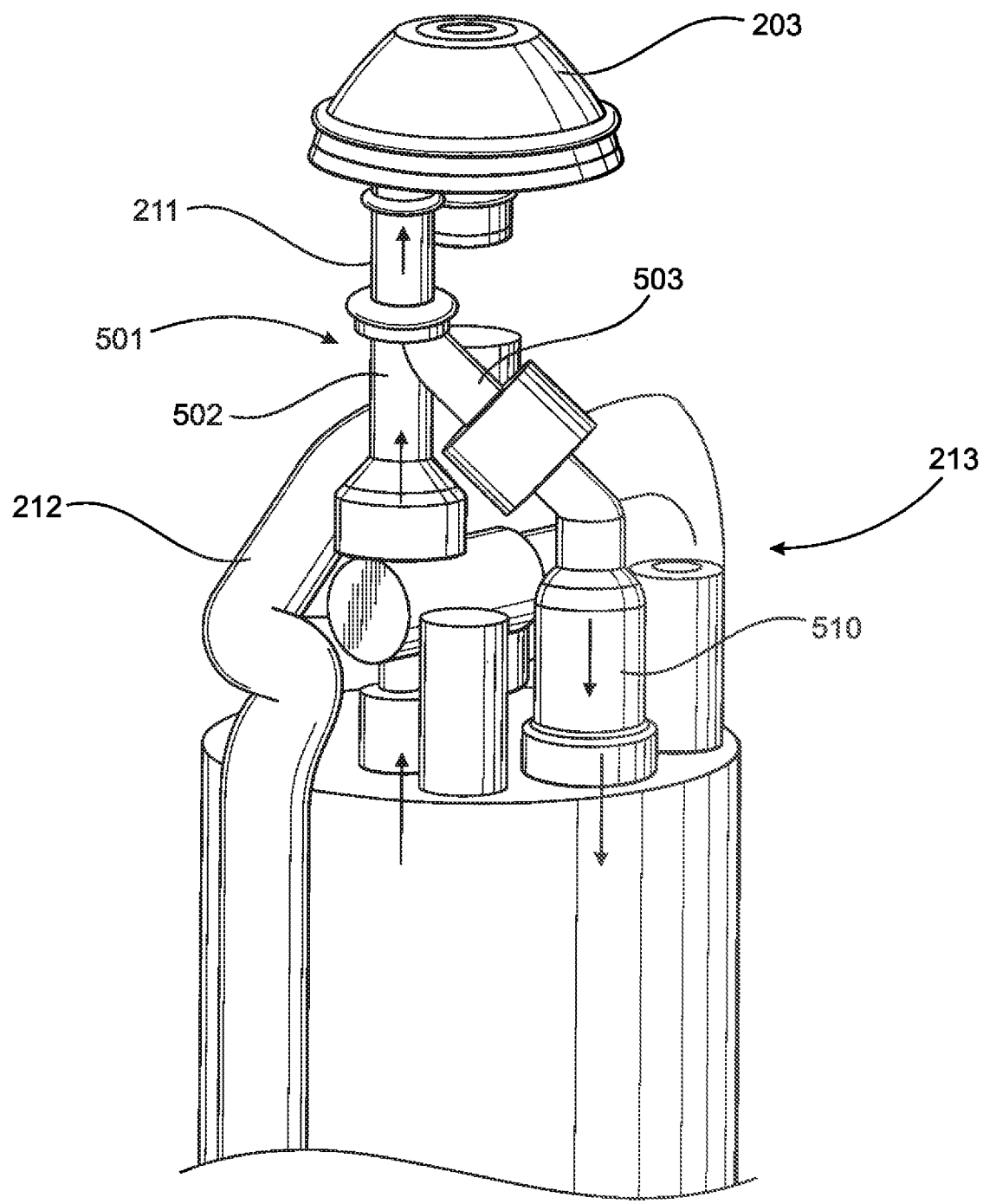
FIG. 14 is a perspective view of the valve assembly of the nasal irrigation assembly.
Figure 15A:
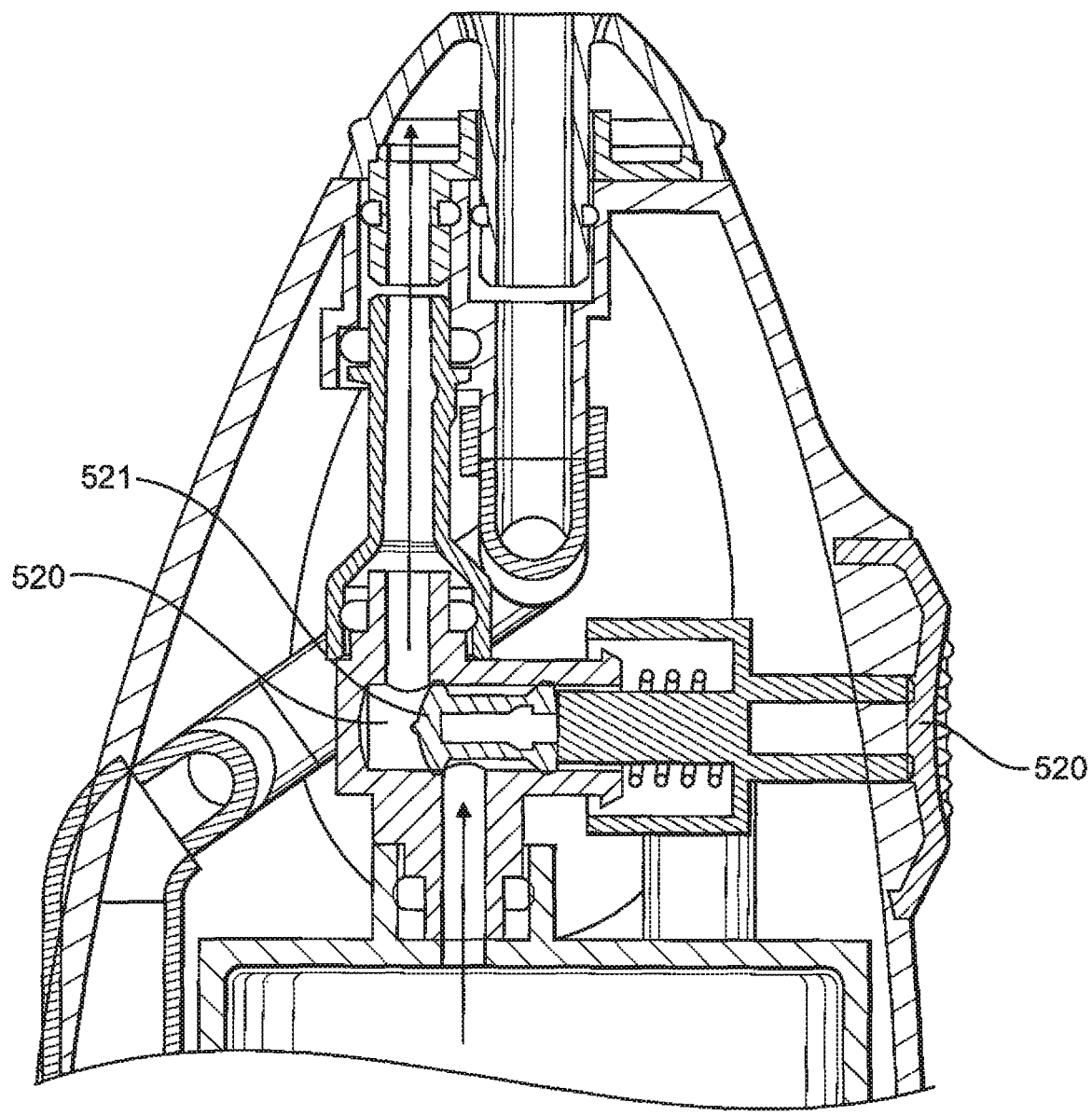
FIG. 15A is a detail side cutaway view of an embodiment of the valve assembly of the nasal irrigation assembly.
Figure 15B:
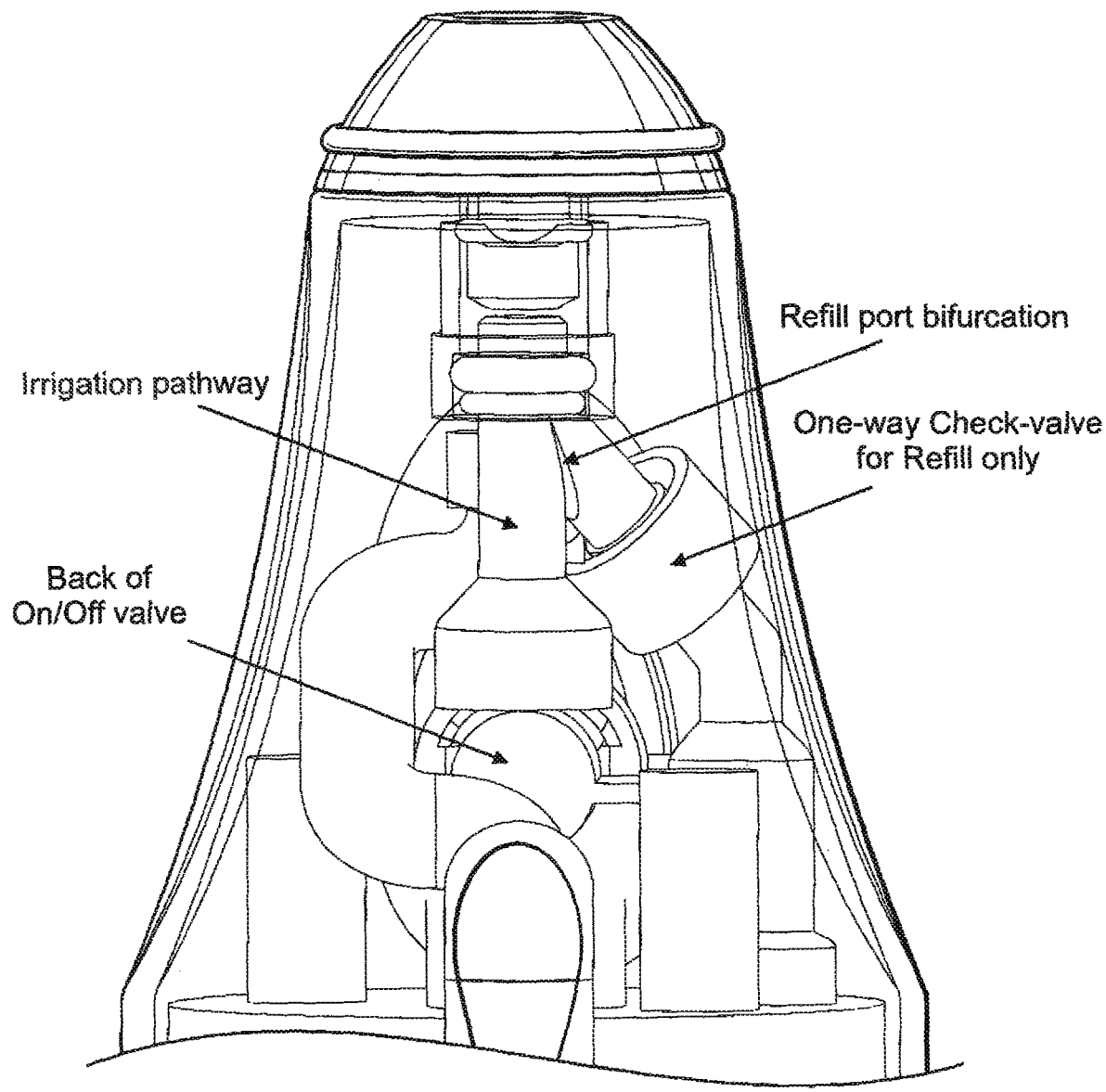
FIG. 15B is a detail back cutaway view of an embodiment of the valve assembly of the nasal irrigation assembly.

In at least one embodiment, valve assembly 213 may comprise additional components as illustrated in FIGS. 13-15. According to FIG. 13B, valve assembly 213 may comprise a bifurcated structure 501 comprising an irrigation segment 502 and a refill segment 503. The irrigation segment 502 may be operatively structured and connected to an irrigation control 520 and define a path of fluid flow of the irrigating solution from the irrigation control 520 to the applicator 203. Similarly, the refill segment 503 may be operatively structured and connected to a refill control 510 and define a path of fluid flow of the irrigating solution from the solution port to the refill control 510.

The irrigation control 520, as illustrated in FIGS. 13B and 15A in various embodiments, may be disposable between an irrigation position (on position) and an off position. The irrigation position may define a path of fluid flow of the irrigating fluid from the refill chamber 202, through the irrigation segment 502 of the bifurcated structure 501, into the applicator 203, and out of the plurality of apertures 250. The off position of the irrigation control 520, on the other hand, prevents irrigating fluid from entering into the irrigation segment 502 of the bifurcated structure 501. The irrigation control 520 may comprise a stopper 521 as illustrated in FIG. 15A, which may be disposable between an irrigation position, and the off position, and may be controlled through user interface 220. For instance, the irrigation control 520 may change from the irrigation position to the off position when the user interface 220, as illustrated in FIG. 15A is pressed or depressed.

The refill control 510 may be disposable between a refill position and an original position. The refill position may define a path of fluid flow of the irrigating fluid from a refill dispenser into the solution port 211 down to the refill segment 503 of the bifurcated structure 501, and into the refill chamber 202. The original position, on the other hand, may prevent irrigating fluid from entering into the refill chamber 202. In at least one embodiment, refill control 510 may comprise a check valve 511, and more particularly may comprise a ball 512 of the check valve 511 which may be spring loaded. As such, when sufficient pressure is exerted upon the ball 512 of the check valve 511 to overcome the force exerted by the spring, the ball 512 moves and the valve opens, thus automatically transitioning into the refill position. In other embodiments, other types of check valves may be utilized, such as a diaphragm check valve, a swing check valve, a stop-check valve, a lift-check valve, as well as other valves or components appropriate for facilitating the one-way fluid flow of the irrigating fluid.

Figure 16:
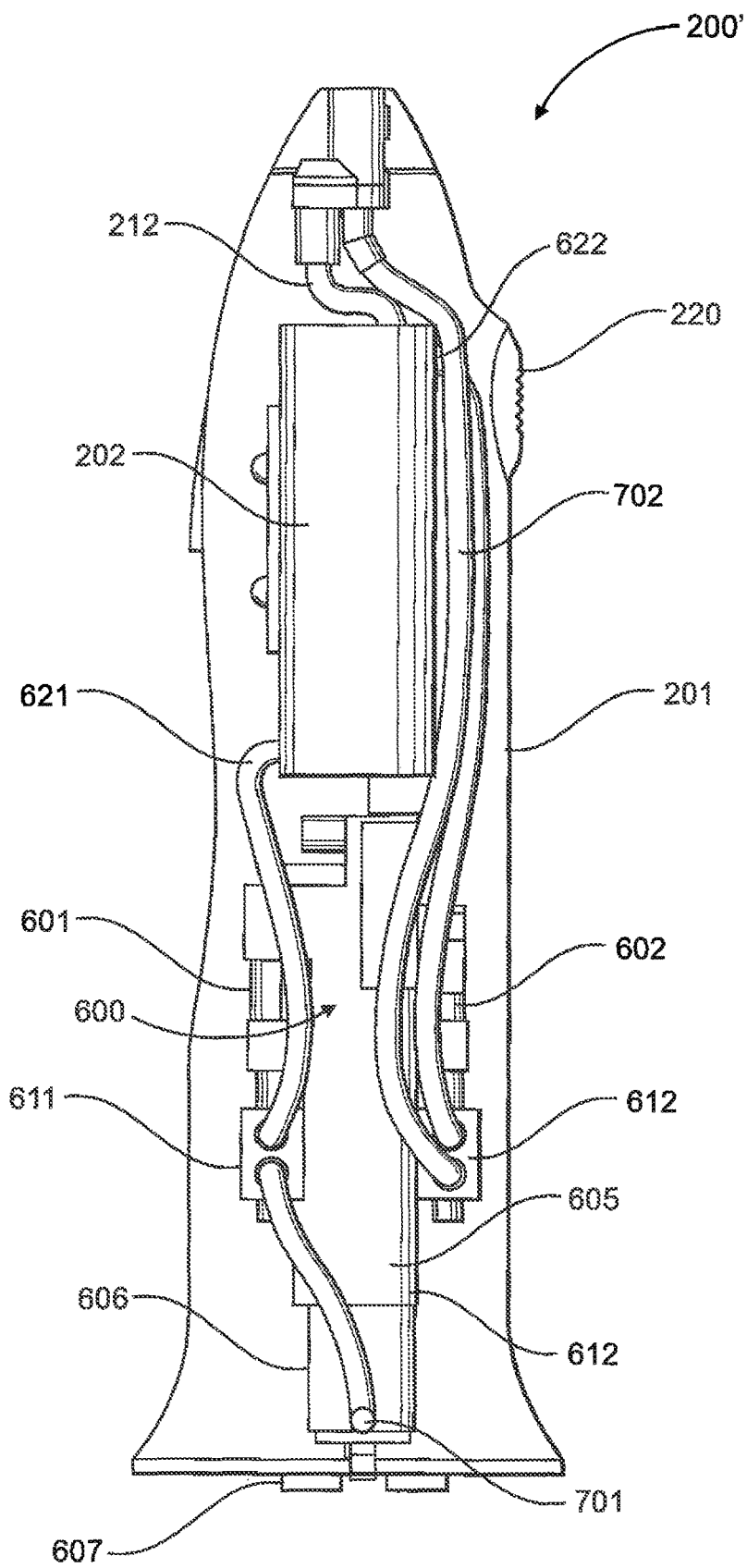
FIG. 16 is a cutaway view of an embodiment of the nasal irrigation assembly comprising a fluid pump.

Of course, rather than having a single solution port, another embodiment of the present invention, such as in FIG. 16, may comprise a refill port for refilling irrigating fluid into the handheld irrigator, and a separate irrigation port for forcing the irrigating fluid out of the handheld irrigator. In these embodiments at least a portion of valve assembly 213 may be omitted and/or the valve assembly 213 may comprise a plurality of different valves which may be used to accompany the inlet and outlet of the separate ports.

The actuator 204 may comprise a fluid pump, such as a peristaltic pump or any other positive displacement pumps. In other embodiments, the delivery assembly 103 may comprise impulse pumps, diaphragm pumps, bellow pumps, impeller pumps, velocity pumps, gravity pumps, steam pumps, valveless pumps, or any other pumps or other device appropriate for creating liquid flow or movement. The actuator 204 may be powered by an internal power supply, which may be rechargeable and/or battery powered, but also be tethered to an external power supply. In other embodiments, the actuator 204 may also comprise a spring-driven piston as illustrated in FIG. 13A as 204', which may include a spring loaded mechanism and a plunger, a manually driven piston not shown, or other piston and/or plunger driven by pressure, such as from a CO2 canister.

In the embodiment of FIG. 13A, the actuator 204' may be cooperatively structured with user interface 220, such that the pressing or depressing of a button may unlock the spring driven plunger in order to create a pressurized flow from the refill chamber 202 out through the applicator 203. In a preferred embodiment, outgoing pressure of the irrigating fluid from the refill chamber 202 may range from 11 psi to 15 psi. During the refill of the irrigating fluid, pressures exceeding 28 psi may unseat rubber plunger in order to compress and/or reset the spring. Of course, other pressures may be utilized depending on the spring tension and/or type of spring used. In some embodiments, the docking station 100 and/or solution assembly refills the handheld irrigator by a predetermined amount in order to fully compress the spring. In other embodiments, the refilling may stop automatically when the spring is fully compressed such as via a mechanical mechanism or an electrical, infrared, or other sensor.

Figure 6:
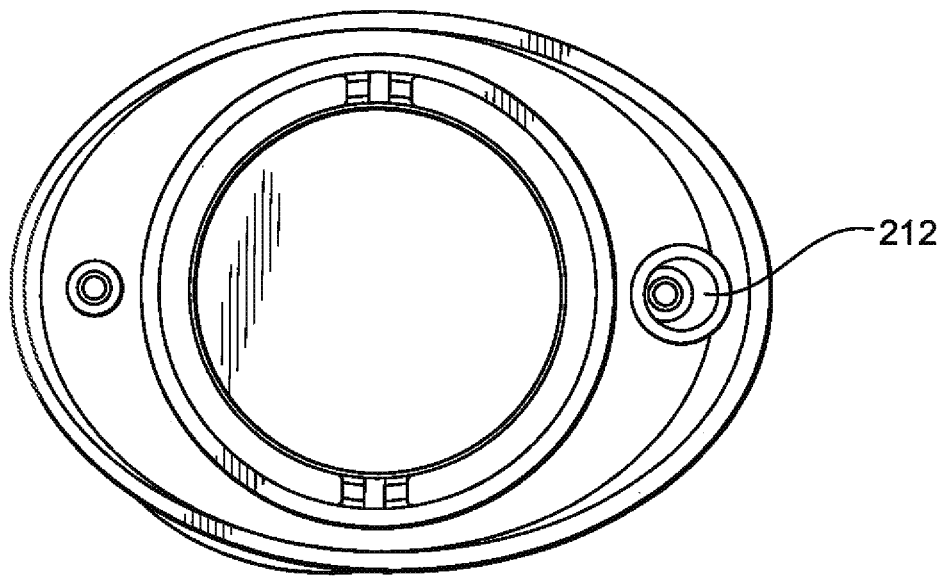
FIG. 6 is a bottom plan detail view of the nasal irrigation assembly.
Figure 7:
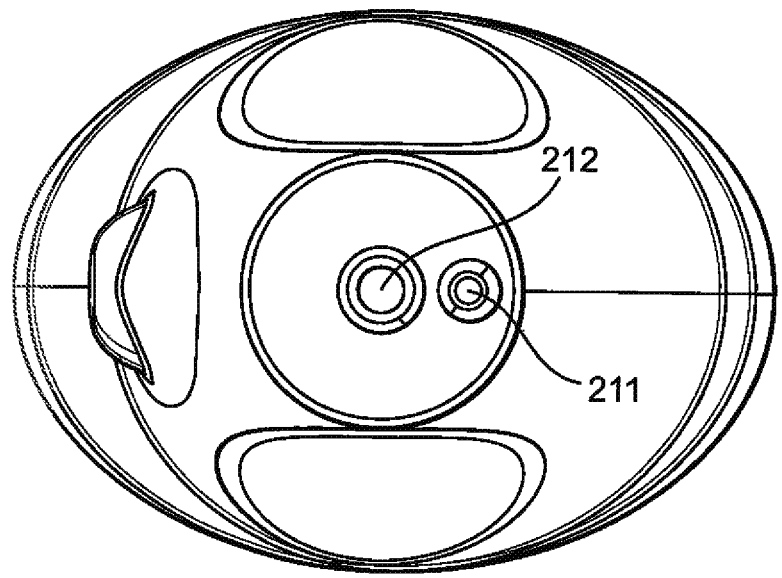
FIG. 7 is a top plan detail view of the nasal irrigation assembly with the applicator removed.
Figure 8:
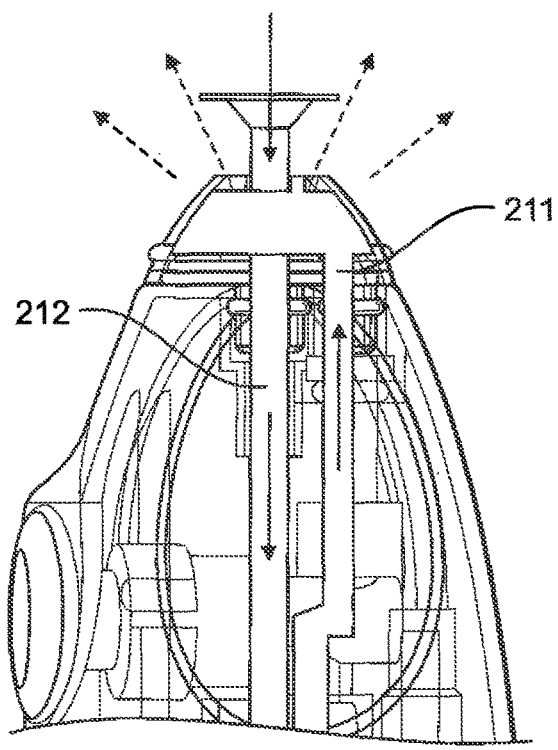
FIG. 8 is a detail cutaway view of the embodiment of FIG. 5 illustrating fluid flow.
Figure 9:
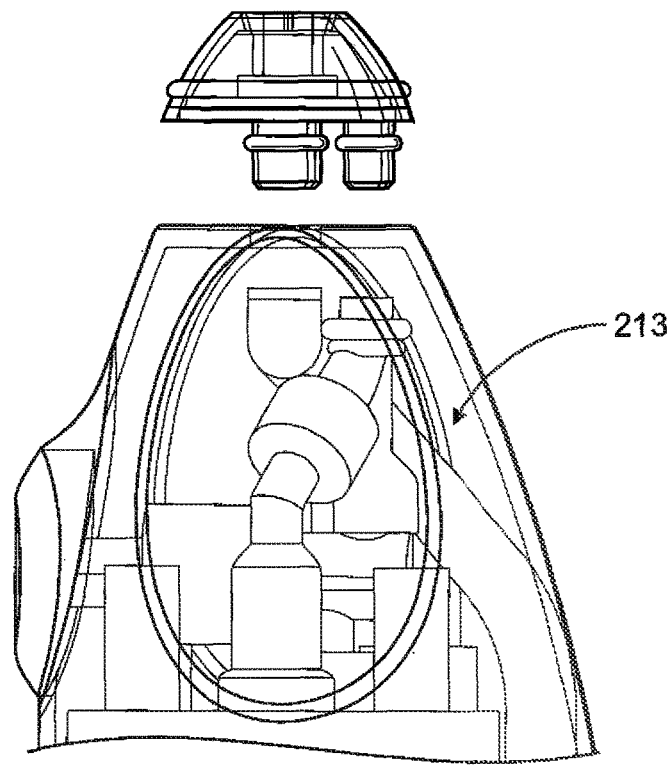
FIG. 9 is a detail cutaway view of the embodiment of FIG. 5 illustrating the valve assembly.
Figure 10:
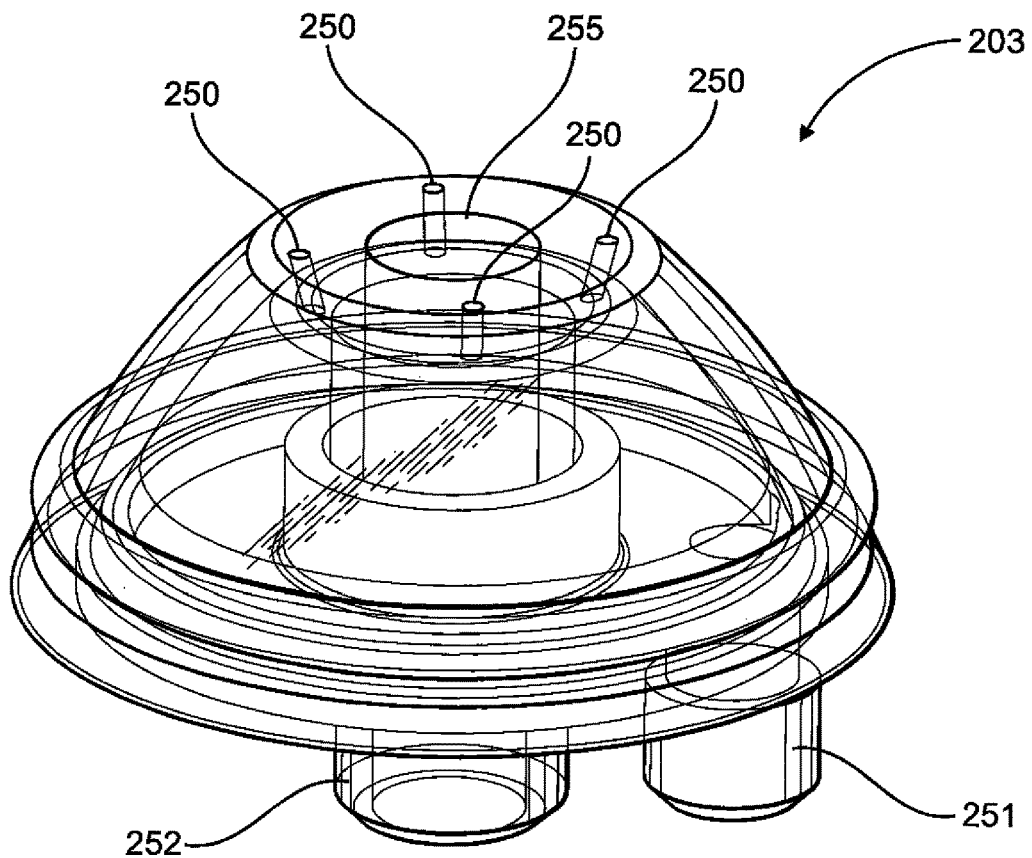
FIG. 10 is a perspective view of an applicator of the nasal irrigation assembly.
Figure 12:
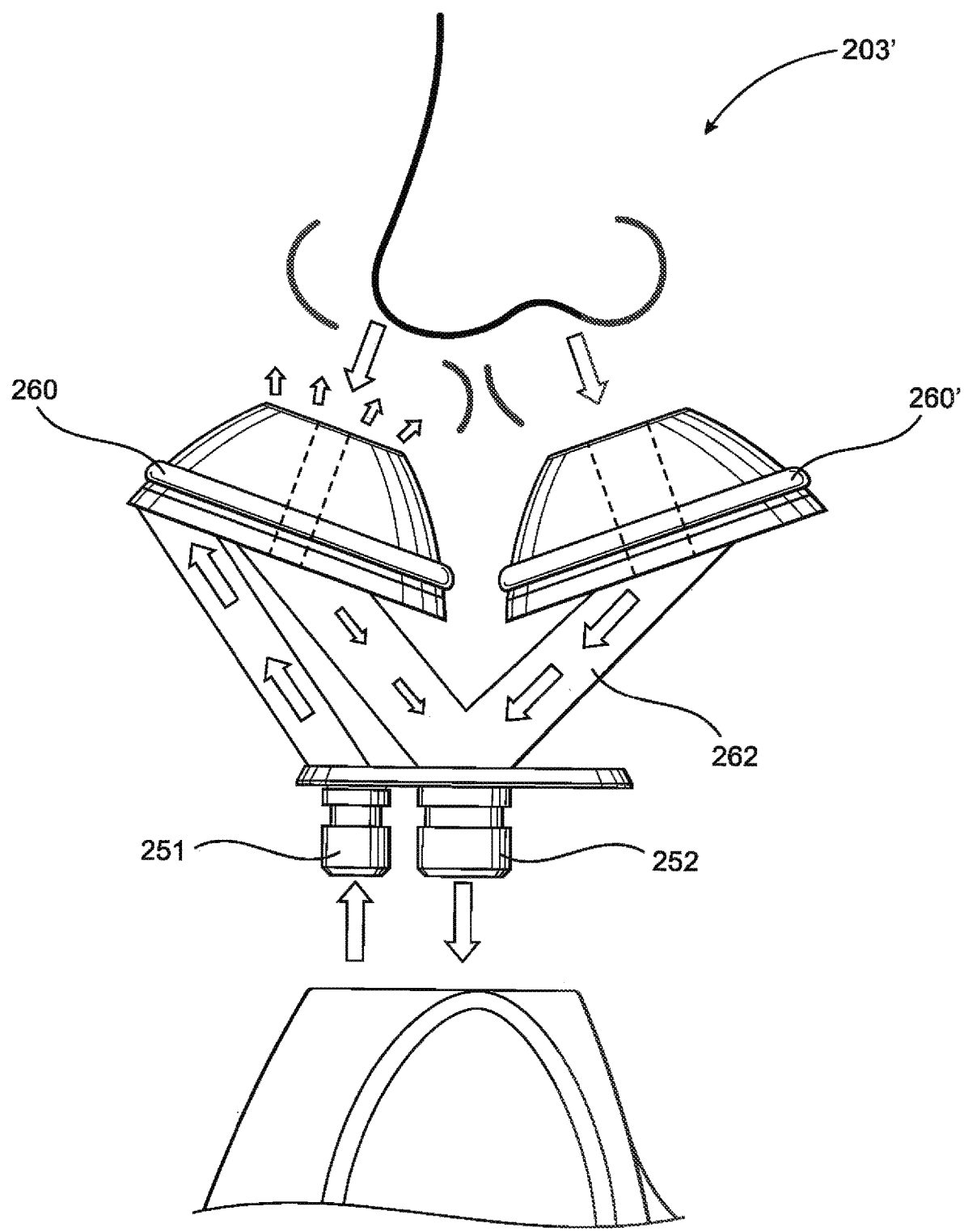
FIG. 12 is a schematic view of another embodiment of the applicator of the nasal irrigation assembly representing intended flow of irrigating fluid and waste fluid during operation.

As schematically represented in FIGS. 8, 10, and 12 and discussed in greater detail hereinafter, waste fluid that does drain back down through a user's nasal cavity and nostril(s) may be collected by the applicator through aperture 255 and drained down through a drain outlet 252 of the applicator 203, then through a separate drain line 212 to be dispersed outside the housing 201. This may allow a user to effectively and easily use the handheld irrigator over a sink. In at least one embodiment the drain line 212 runs down the length of the housing 201 and drains out the bottom of the housing as shown in FIG. 6, which may then fall conveniently into a sink. Alternatively, an additional liquid repository which is not shown may further be utilized to collect the waste fluid which may be removably connected to the housing 201, to facilitate portable use and/or a sample collection for laboratory testing. In other embodiments the drain line 212 may exit elsewhere through the housing 201, which may further minimize spray or splatter to the user.

In some embodiments of the present invention, a diagnostic porous material, not shown, may be used to facilitate testing. For example, a paper strip with a reagent-containing matrix layered thereon or incorporated therein may be vertically positioned so that a small section of the strip is exposed to the waste fluid as it is collected in the liquid repository or otherwise drains down through the handheld device. As such, the paper strip may comprise a diagnostic paper or indicator strip which changes colors in a window visible to the user to indicate whether any infectious agent is identified within the waste fluid. For example, to identify the infectious agent *Bordetella Pertussis* (BP), the paper strip may comprise anti-BP antibodies which is capable of recognizing a single molecule moiety or epitope on BP molecules. The antibodies, for example, may be monoclonal antibodies. Examples of monoclonal antibodies against BP may include monoclonal antibody MAb 2A12, which binds the amino acids 399/623 or 781/828 of adenylate cyclase toxin (AC toxin) of BP, and anti-ptxA antibody, which binds to BP toxin subunit 1. The anti-BP monoclonal antibodies are conjugated with chromogenic or fluorescent dyes as labels to generate signals such as color change on the paper strip.

Figure 11:
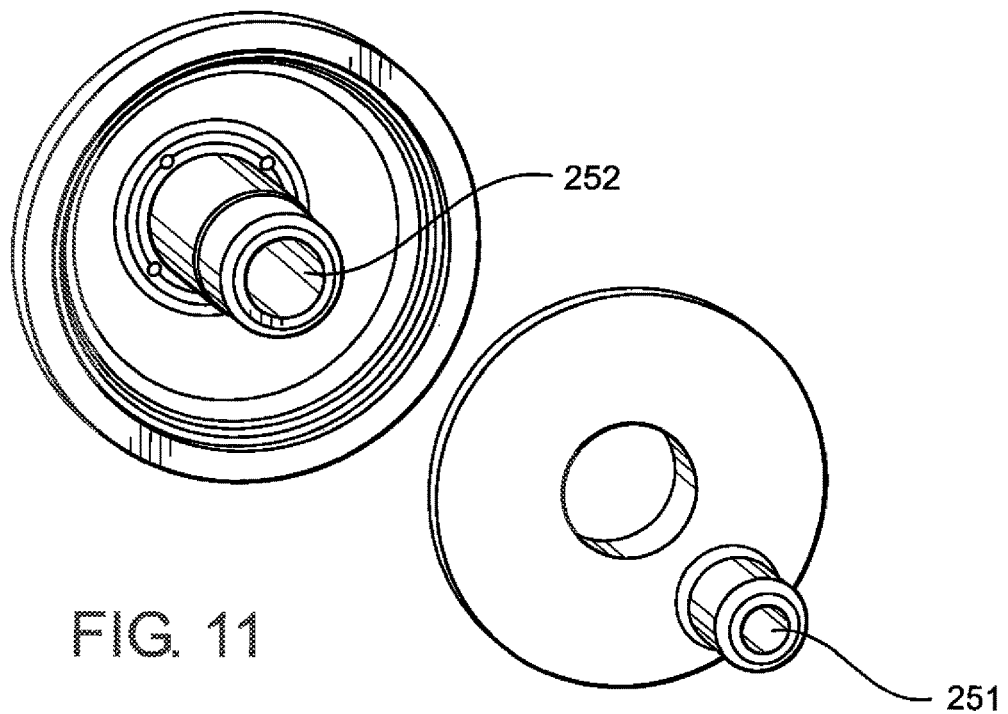
FIG. 11 is a perspective view of components of the applicator of FIG. 10 interior end view of the embodiment.

In at least one embodiment of the present invention, the applicator 203 is removably connected to the housing 201. As such, the applicator 203 may be removed and replaced at will, for instance, separate applicators 203 may be color coded for separate users. Applicators 203 may comprise both single nostril embodiments as illustrated in FIGS. 10 and 11, as well as dual nostril embodiments as illustrated in FIG. 12. In the embodiment of FIG. 12, a similar irrigation inlet 251 and drain outlet 252 exists as in the single nostril embodiment. However, drainage is now received from both nostrils via a first tip 260 and a second tip 260', and waste fluid is passed down from both tips into the passage assembly 262. In at least one embodiment, the draining aperture of one tip may be smaller than the other tip. In another embodiment, drainage may be possible on via one of the two tips. These embodiments may be utilized in order to create a "flooding" flow. This may allow the irrigating fluid to enter through one nostril and out the other, in order to clean and irrigate the entire nasal cavity of a user. In some embodiments of the present invention, the irrigating fluid may be supplied to a user's nostril concurrently to the waste fluid being drained and removed therefrom.

A user interface 220 of the handheld irrigator 200 may allow a user to enable and disable the operation of the handheld irrigator 200, as well as effect operations of the actuator 204. The user interface 220 may comprise controls to adjust the actuator 204 in order to change or adjust the rate of flow of the irrigating fluid during operation, the time, as well as pulsation. The user interface 220 may additionally allow a user to reverse the direction of flow of the irrigating fluid, and this may allow a user to refill a handheld irrigator 200 from a refill dispenser.

Another embodiment of the handheld irrigator 200' is depicted in further detail in FIG. 16. Accordingly, the handheld irrigator 200' may comprise a similar housing 201 as the above embodiments, a refill chamber 202, an applicator 203 not shown, an actuator 600 comprising a fluid pump, a drain line 212, a valve assembly 213, and a user interface 220. Rather than having a single solution port, the handheld irrigator 200' may comprise a separate refill port 701 and irrigation port and/or irrigation line 702. The refill port 701 may be located at the base of the handheld device 200', or may alternatively be located at the apical portion of the handheld device 200' as the above embodiments.

In at least one embodiment, the handheld irrigator 200' comprises an inlet valve assembly 611 and an outlet valve assembly 612 selectively or collectively disposable between an irrigation position and a refill position. The refill position defines a path of fluid flow of irrigating solution from the refill port 701 through the inlet valve assembly 611, outlet valve assembly 612, and finally into the refill chamber 202 through chamber inlet 622. The irrigation position defines a path of fluid flow of irrigating solution from the refill chamber 202 out from chamber outlet 621, through the inlet valve assembly 611, outlet valve assembly 612, and finally out through the irrigation line 702.

The flow of the irrigating solution may be controlled by actuator 600 which may comprise a fluid pump as discussed above. Actuator 600 may further comprise a motor 605, powered by battery 606, which may further be rechargeable via charging contacts 607. Accordingly, actuator 600 may further comprise a pump inlet 601 which creates a suction force allowing irrigating fluid to enter the pump, and a pump outlet 602 that discharges the irrigating fluid in order to create the flow of the irrigating fluid.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An assembly for nasal irrigation comprising:
a housing including a refill chamber structured to contain irrigating fluid therein,
an applicator connected to said housing in fluid communication with said refill chamber and the irrigating fluid,
an actuator structured and disposed to initiate the passage of the irrigating fluid from said refill chamber through said applicator and into a user's nasal cavity,
a solution port structured and disposed to receive irrigating fluid from a refill dispenser into said refill chamber, said solution port further structured and disposed to direct irrigating fluid from said refill chamber to said applicator,
a valve assembly disposable between an irrigation position and a refill position;
said irrigation position defining a path of fluid flow of the irrigating fluid from said refill chamber to said applicator, and into the user's nasal cavity;
said refill position defining a path of fluid flow of the irrigating fluid from the refill dispenser into said refill chamber,
said valve assembly further comprising a refill control including a check valve,
said refill control and check valve disposable between said refill position and an original position, said original position preventing fluid flow of the irrigating fluid into said refill chamber, and
said refill control automatically transitions into said refill position when a predetermined amount of fluid pressure is applied to said refill control.

2. The assembly as recited in claim 1 wherein said actuator is cooperatively structured and disposed with said valve assembly to force the irrigating fluid from said refill chamber through said applicator, when said valve assembly is in said irrigation position.

3. The assembly as recited in claim 1 wherein said actuator is cooperatively structured and disposed with said valve assembly to draw the irrigating fluid from the refill dispenser into said refill chamber, when said valve assembly is in said refill position.

4. The assembly as recited in claim 1 wherein said valve assembly further comprises an irrigation control disposable between said irrigation position and an off position, wherein said off position prevents the fluid flow of the irrigating fluid from said refill chamber.

5. The assembly as recited in claim 1 wherein said valve assembly comprises an irrigation segment and a refill segment, said irrigation segment operatively structured and connected to said irrigation control and defining a path of fluid flow of the irrigating fluid from said irrigation control to said applicator; and said refill segment operatively structured and connected to said refill control and defining a path of fluid flow of the irrigating fluid from said solution port to said refill control.

6. The assembly as recited in claim 1 wherein said applicator comprises an irrigation inlet, said irrigation inlet at least partially defining a flow path of the irrigating fluid from said refill chamber into the user's nasal cavity.

7. The assembly as recited in claim 6 wherein said applicator further comprises a drain outlet for receiving waste fluid from the user's nasal cavity.

8. The assembly as recited in claim 7 further comprising a drain line connected to and in fluid communication with said drain outlet, said drain line disposed and structured to dispense the waste fluid to an exterior of the housing.

9. The assembly as recited in claim 8 wherein said drain line exits a bottom of said housing.

10. The assembly as recited in claim 8 wherein said drain line exits into a waste liquid repository removably connected to said housing.

11. The assembly as recited in claim 1 wherein said applicator is removably connected to said housing.

12. The assembly as recited in claim 1 wherein said applicator comprises two tips structured to concurrently engage both nostrils of the user.

13. The assembly as recited in claim 1 wherein said actuator comprises a spring driven piston.

14. The assembly as recited in claim 1 wherein said actuator comprises a fluid pump.

15. The assembly as recited in claim 1 wherein said actuator comprises a peristaltic pump.

16. The assembly as recited in claim 1 further comprising a user interface operatively structured and configured to adjust said actuator in order to change the rate of flow of the irrigating fluid.

* * * * *